(12) United States Patent
Dickie et al.

(10) Patent No.: US 9,717,654 B2
(45) Date of Patent: Aug. 1, 2017

(54) ELECTRONIC PILL BOX PREFILL SYSTEM INCLUDING A BLISTER PACK WITH A CAPACITIVE SENSOR

(71) Applicant: Next Paradigm Inc., Toronto (CA)

(72) Inventors: Robert G. Dickie, King City, CA (US); Walter Prokopchuk, King City, CA (US)

(73) Assignee: Next Paradigm Inc., Toronto, Ontario (CA)

( * ) Notice: Subject to any disclaimer, the term of this patent is extended or adjusted under 35 U.S.C. 154(b) by 0 days.

(21) Appl. No.: 14/858,041

(22) Filed: Sep. 18, 2015

(65) Prior Publication Data

US 2016/0000657 A1    Jan. 7, 2016

Related U.S. Application Data

(63) Continuation-in-part of application No. 13/965,966, filed on Aug. 13, 2013, now Pat. No. 9,311,452.

(51) Int. Cl.
| | |
|---|---|
| G08B 21/00 | (2006.01) |
| A61J 7/04 | (2006.01) |
| A61J 7/00 | (2006.01) |
| A61J 1/03 | (2006.01) |

(52) U.S. Cl.
CPC ............ *A61J 7/0481* (2013.01); *A61J 7/0084* (2013.01); *A61J 7/0436* (2015.05); *A61J 1/035* (2013.01); *A61J 7/0418* (2015.05); *A61J 2200/30* (2013.01); *A61J 2205/20* (2013.01)

(58) Field of Classification Search
CPC .................................. A61J 7/04; A61J 7/0409
USPC ................ 340/309.7, 573.1, 309.16; 368/10; 221/2; 206/534
See application file for complete search history.

(56) References Cited

U.S. PATENT DOCUMENTS

| | | |
|---|---|---|
| 3,762,601 A | 10/1973 | McLaughlin |
| 4,275,384 A | 6/1981 | Hicks et al. |
| 4,382,688 A | 5/1983 | Machamer |
| 4,748,600 A | 5/1988 | Urquhart |
| 5,020,037 A | 5/1991 | Raven |

(Continued)

FOREIGN PATENT DOCUMENTS

| | | |
|---|---|---|
| CN | 103315909 | 9/2013 |
| FR | 2892016 | 4/2007 |

(Continued)

*Primary Examiner* — Jeffery Hofsass
(74) *Attorney, Agent, or Firm* — Sand & Sebolt

(57) ABSTRACT

An electronic pill box having a housing with a base and grid and into which a blister pack is selectively engaged. The blister pack includes a plurality of vials prefilled with medication and sealed with a cover imprinted with pertinent information. Each vial is received in a chamber in the base having an LED and a sensor for determining whether medication has been removed therefrom. The LED and sensor are operatively engaged with a microprocessor including programming for dispensing medication from the pill box. An alert is issued if medication is not removed from an illuminated vial after a predetermined time interval. When all medication has been dispensed therefrom, the blister pack is replaced with another prefilled blister pack A card with patient information thereon may be provided on the prefilled blister pack and is detached and stored in the housing prior to loading the blister pack therein.

18 Claims, 18 Drawing Sheets

(56) References Cited

U.S. PATENT DOCUMENTS

| | | | |
|---|---|---|---|
| 5,099,463 A | 3/1992 | Lloyd et al. | |
| 5,200,891 A | 4/1993 | Kehr et al. | |
| 5,850,937 A | 12/1998 | Rauche | |
| 6,048,087 A | 4/2000 | Laurent et al. | |
| 2003/0080854 A1 | 5/2003 | Brakus | |
| 2005/0075908 A1 | 4/2005 | Stevens | |
| 2010/0314282 A1 | 12/2010 | Bowers | |
| 2011/0155602 A1* | 6/2011 | Sterry | A61J 7/0436 206/459.1 |
| 2012/0006708 A1 | 1/2012 | Mazur | |
| 2013/0222135 A1* | 8/2013 | Stein | A61J 7/0409 340/540 |

FOREIGN PATENT DOCUMENTS

| | | |
|---|---|---|
| WO | 0217850 | 3/2002 |
| WO | 2012111034 | 8/2012 |
| WO | 2013071225 | 5/2013 |

\* cited by examiner

ELECTRONIC PILL BOX PREFILL SYSTEM INCLUDING A BLISTER PACK WITH A CAPACITIVE SENSOR

CROSS-REFERENCE TO RELATED APPLICATIONS

This is a Continuation-in-Part of U.S. patent application Ser. No. 13/965,966, filed Aug. 13, 2013, the entire specification of which is incorporated herein by reference.

BACKGROUND OF THE INVENTION

Technical Field

This invention relates generally to pill boxes for storing several different medications. More particularly, this invention relates to an electronic pill box. Specifically, this invention is directed to an electronic pill box and a method of using the same where the pill box includes a housing having a base and a grid; and a blister pack including a plurality of vials prefilled with medication, where the vials are positioned adjacent an illumination source and a sensor connected to a microprocessor when the blister pack is engaged in the housing.

Background Information

Doctors prescribe medication for patients suffering from a variety of illnesses. One of the issues that is fairly common is that patients frequently do not follow the exact dosage regimen prescribed by the physician. They will tend to forget to take a dose at a prescribed time or will accidentally double up dosages when they can't remember if they took the medication at the prescribed time. Because the prescribed regimen is not being followed, the healing which should occur through action of the medication on their body may be slowed or the patient could actually put their health in jeopardy by overdosing themselves.

There have been attempts in the prior art to develop some type of system to assist a patient in keeping prescribed medication regimens. For example, U.S. Pat. No. 3,762,601 (McLaughlin) discloses a cabinet that has several independent vials into which individual doses of medication are placed. The cabinet includes some type of timing mechanism which automatically opens a locking mechanism engaged with a door to a particular vial when a preset time arrives. The locking mechanisms are timed for a twenty four hour period and the system includes a main signal light on the side of the cabinet to alert a caregiver that it is time to dispense medication to the patient. A keyed master-door blocks access to individual vial doors. A light is also associated with each vial in the cabinet and, if a vial is unlocked, the associated light will be illuminated to indicate the unlocked condition of the vial. The downfall with this system is that the master door has to be unlocked by a person other than the patient, such as a nurse. If the nurse does not unlock the master door then there will be no access to the unlocked vial. If the master door is unlocked and a vial door is automatically unlocked and opened at the preset time and the patient is not in any condition to access the medicine in the vial, that medicine could be accessed by other persons, such as children. Additionally, this type of cabinet is not designed to be carried around by the patient. It is configured to be mounted permanently on a wall, for example.

Hicks (U.S. Pat. No. 4,275,384) discloses a portable medicine cabinet with a computerized timer. Predetermined time intervals are entered into the computerized timer. The timer is connected to an indicator mechanism that indicates the predetermined time intervals and which of the medicines should be removed from vials within the cabinet. Each vial in the cabinet is cylindrical in shape and has a hinged door positioned to close off access to the vial. A means for entering time into the computer is provided on the cabinet. The computer generates an output signal when a present time is reached and this signal causes a signal light provided on the exterior surface of the cabinet proximate a vial to become illuminated. This lets the patient know which medicine to take. The cabinet also includes a screen for displaying time and a digital number for the vial to be accessed. The cabinet also includes a buzzer to alert the patient that it is time to take a medicine from the indicated vial.

U.S. Pat. No. 4,382,688 (Machamer) discloses a portable medical dispenser that includes a door which is retained in a closed position by way of a latch. The system includes a timer and an electronic memory. When a preset time is reached an audible alarm is sounded to notify the user that it is time to take a medication within the dispenser. The alarm may also include a flashing of the time display on the dispenser. A switch is mounted adjacent the door latch to detect when the door is opened. A disarming mechanism is provided and is capable of being programmed to disarm the alarm for a particular period. This is utilized when the portable dispenser is used for retaining birth control pills and no reminders to the user are needed for several days each month. The electronic memory cannot be altered by the user.

Urquhart (U.S. Pat. No. 4,748,600) discloses a dispenser that controls doses of pharmaceuticals to a patient. The dispenser includes a central processing unit that is programmed with an initial dosing regimen and is able to record and monitor dispensing of pharmaceuticals from the dispenser. The dispenser includes a timer and means for recording the actual times medicines are dispensed and for calculating discrepancies between the prescribed dispensing time and the actual dispensing time. The dispenser further includes a means for calculating a dosing correction factor for the patient based on the information gathered by the dispenser. The dispenser includes a display screen for displaying information it gathers and calculates. The patient is able to input information into the dispenser to be used in the various calculations performed by the dispenser. The dispenser is also equipped to provide a physician with information regarding any deviations in the dosing regimen.

Raven (U.S. Pat. No. 5,020,037) discloses a pill box that includes a timer to track time and an alarm to notify a patient when to take medication retained within the pill box at particular preset times. The alarm is deactivated when a door to a vial in the pill box is opened. The pill box includes an electronic memory that records each time the alarm is canceled and a display screen capable of displaying the recorded information. The times set in the timer can only be adjusted if the door to a vial is in the open position.

U.S. Pat. No. 5,099,463 to Lloyd et al discloses a medicine dispenser that includes a timer and a display for indicating the time at which a particular medicine should be taken and for giving the patient visual instructions. The dispenser is configured so that the medication can be kept in the original containers provided by a pharmacist. The dispenser is programmed to queue the medications so that they are able to be taken in the correct sequence. Sensors are provided in the various vials of the dispenser to verify that medication containers are returned to the dispenser after use. An alarm system is also provided in the dispenser to alert the patient that it is time to take a medicine from one of the vials. The alarm system generates a sound and/or illuminates a light to alert the patient that action must be taken.

Kehr et al (U.S. Pat. No. 5,200,891) discloses a medication dispenser having a programmable microprocessor and a number of vials, each of which may store medication. A signaling system is provided to alert the patient to the fact that medication should be taken, to identify which vial the medication should be removed from; and the quantity of medication that is to be taken at that specific time. An alarm will sound if the designated vial is not opened within a certain period of time. The alarm is disarmed if the vial door is opened. The dispenser includes a display screen for displaying pertinent information. The device also includes a means for the patient to program the microprocessor.

U.S. Pat. No. 5,850,937 (Rauche) discloses a dispenser that is capable of alerting a patient that it is time to take a medication from one of a plurality of vials. The dispenser includes a real-time clock for tracking time and a memory for storing times for taking medication. There is also an input for entering the times to be stored in the memory and an alarm system that is activated when the tracked real time corresponds to the stored time for taking medication. The dispenser housing is transparent so that a medication summary sheet retained within a vial is visible when the vial is closed. There are mounting devices within the vials for retaining an inhaler in a particular orientation therein. The door for each vial is locked into placed by an electronic mechanism and the door can only be moved to an open position when the electronic mechanism is deactivated. The dispenser also includes a real-time clock, a display, a push-button matrix for entering a code sequence, a buzzer, a light, and a vibratory mechanism; the last three components being provided to selectively alert a patient that it is time to take a medication from the dispenser. The dispenser also includes a programmable memory and control means for controlling various components that make up the dispenser.

Finally, U.S. Pat. No. 6,048,087 (Laurent et al) discloses an electronic pill box that includes multiple vials for retaining doses of medicine therein. The pill box includes a microprocessor that can have prescription data inputted therein. A display is provided on the device and each vial has a pill dispenser that is adapted to dispense pharmaceuticals of various forms and sizes therefrom. An automatic controller associated with each vial controls medication movement from the vial. Data can be loaded into the microprocessor by a detachable data medium. The system also includes a detector associated with each vial and the memory records the withdrawal of pills from each vial. The microprocessor includes a counter responsive to the detector for counting down the pills dispensed from the vial. This enables the patient to determine the remaining number of medications in each vial. The vials are selectively detachable from the dispenser and the dispenser's controller is capable of determining how many vials are engaged with the dispenser's housing at any time.

BRIEF SUMMARY OF THE INVENTION

While all of the above medication dispensers provide various levels of alerts and monitor the dispensing of medication to various degrees, there remains a need in the art for a medication dispenser with an improved reminder system.

An electronic pill box having a housing with a base and grid and into which a blister pack is selectively engaged is disclosed herein. The blister pack includes a plurality of vials prefilled with medication and sealed with a cover imprinted with pertinent information. Each vial is received in a chamber in the base having an LED and a sensor for determining whether medication has been removed therefrom. The LED and sensor are operatively engaged with a microprocessor including programming for dispensing medication from the pill box. An alert is issued if medication is not removed from an illuminated vial after a predetermined time interval. When all medication has been dispensed therefrom, the blister pack is replaced with another prefilled blister pack A card with patient information thereon may be provided on the prefilled blister pack and is detached and stored in the housing prior to loading the blister pack therein. This card may be used as a reference for a caregiver to help them ensure that medication is being given to the correct patient and to determine where to reorder medication or what steps should be taken if the patient exhibits a reaction to the medication. Any other relevant information may be provided on this card.

In one aspect the invention may provide a medication reminder and compliance system comprising a pill box including a housing; a microprocessor including programming that includes a reminder schedule and a real time tracker;

a blister pack selectively receivable within the housing; said blister pack including a plurality of vials, each vial being prefilled with medication; and a plurality of sensors provided in the housing, wherein each sensor is located so as to be positioned adjacent a different one of the vials of the blister pack when received within the housing; and wherein each sensor is operatively engaged with the microprocessor.

In another aspect, the invention may provide a method of dispensing medication to a patient comprising providing a pill box including a housing comprising a base and a grid engageable with the base; and a microprocessor including programming that includes a reminder schedule and a real time tracker; providing a blister pack having a plurality of vials defined therein with at least some of the vials being prefilled with medication; and having a cover extending across openings to the plurality of vials, said cover having lines of weakness proximate each vial; positioning the blister pack in the base; engaging the grid with the base; capturing the blister pack between the grid and the base; and activating the microprocessor to initiate the reminder schedule.

BRIEF DESCRIPTION OF THE SEVERAL VIEWS OF THE DRAWINGS

A preferred embodiment of the invention, illustrated of the best mode in which Applicant contemplates applying the principles, is set forth in the following description and is shown in the drawings and is particularly and distinctly pointed out and set forth in the appended claims.

Similar numbers refer to similar parts throughout the drawings.

DETAILED DESCRIPTION OF THE INVENTION

Figure 1:
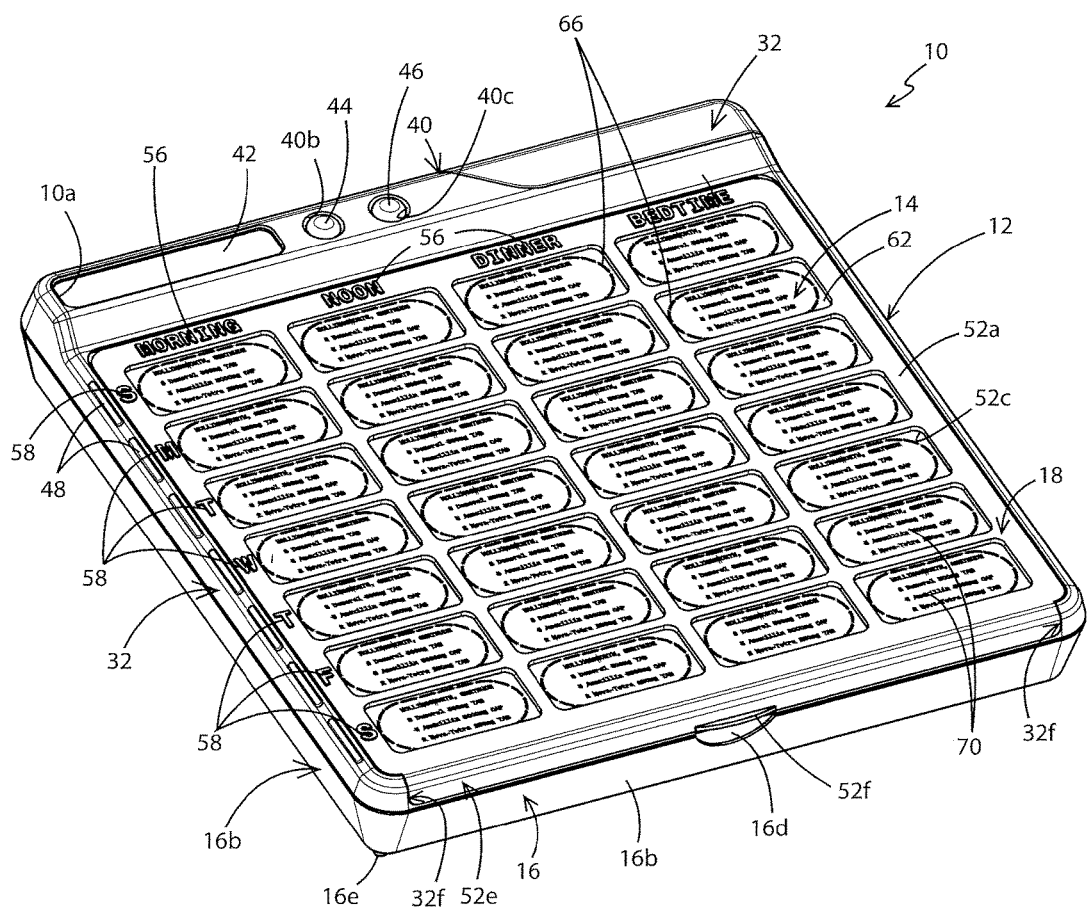
FIG. 1 is a perspective view of a medication reminder and compliance system in accordance with an aspect of the invention, said system including an electronic pill box that is utilized by a patient, where the pill box is illustrated in a closed position.

Referring to FIGS. 1-16 there is shown an electronic pill box, generally indicated at 10. Pill box 10 is used in a medication reminder and compliance system such as the system disclosed in U.S. patent application Ser. No. 13/965, 966 filed Aug. 13, 2013 from which the present application claims priority or the system disclosed in U.S. patent application Ser. No. 13/966,037, filed Aug. 13, 2013 (hereinafter applications '966 and '037) The entire specifications of both of applications '966 and '037 are incorporated herein by reference. Applications '966 and '037 are commonly owned. Applications '966 and '037 disclose in detail how an electronic pill box is contemplated to be used to issue reminders to a patient or a patient's caregiver when to remove medication from the electronic pill box; and furthermore disclose in detail how the electronic pill box will issue reminders, alerts and alarms if it is determined medication has not been removed from the pill box at a pre-programmed intervals. The pill box 10 disclosed herein is contemplated to be used in the same fashion and therefore the actual reminder and alert functions will not be disclosed in greater detail. The system disclosed herein discloses a new way or installing medication into the electronic pill box and a new way of determining whether medication has been removed therefrom.

Pill box 10 in accordance with an aspect of the present invention is an electronic pill box that may be able to be connected via Wi-Fi, Bluetooth technology or any other type of communication system to an electronic device, portable or otherwise, that is used by a patient or by a patient's caregiver, or by a hospital or clinic or other medical institution which may be treating the patient. Suitable devices used by the patient, the patient's caregiver, the hospital or clinic include but are not limited to cell phones, smartphones, computers, tablets, and paging systems.

Applications '966 and '037 disclose a pill box having compartments with openable doors. These pill boxes need to have the patient or a caregiver place the various doses of medication (typically in the form of a pill) into the various compartments and then close those doors. The pill box is then actuated so that electronically controlled reminders will be issued at the relevant times. These reminders help remind the patient to take a dose of medication from a specific compartment that is highlighted by illumination of the same. The patient or caregiver opens the relevant door to access the medication. If the door is not opened in a timely fashion, the system generates an alert that is then sent to a linked electronic device of the patient, caregiver, hospital or clinic. Those linked electronic devices may include a smartphone, computer etc. The pill box may also include an audible alarm for warning appropriate persons that a dose of medication needs to be taken.

The pill box disclosed herein is utilized in a similar fashion as it is linkable to an electronic device of the patient or of a caregiver such as a smartphone, computer etc. Pill box 10 differs from the pill box disclosed in applications '966 and '037 in that pill box 10 comprises a housing 12 and a separate blister pack 14. Blister pack 14 is effectively a tray that is prefilled with medication and is sealed. The filling and sealing of blister pack 14 may occur in a factory or in a pharmacy or any other suitable location and the prefilled and sealed blister pack or a plurality of prefilled and sealed blister packs 14 are marked up with information relating to a specific patient (as will be later described herein) and are shipped and/or delivered to the patient, a caregiver, or hospital or clinic.

When received by the patient or caregiver, the housing 12 is moved to an open position and the prefilled and sealed blister pack 14 is selectively loaded into the housing 12. The housing 12 is closed and latched into place and is then available for use. The manner of prefilling the blister pack 14, loading the prefilled blister pack 14 into housing 12, latching blister pack 14 into place, dispensing medication from the blister pack 14 while retained in the housing 12, and the manner of reminding the patient or caregiver to dispense a particular dose from pill box 10 will be further described herein.

Figure 5:
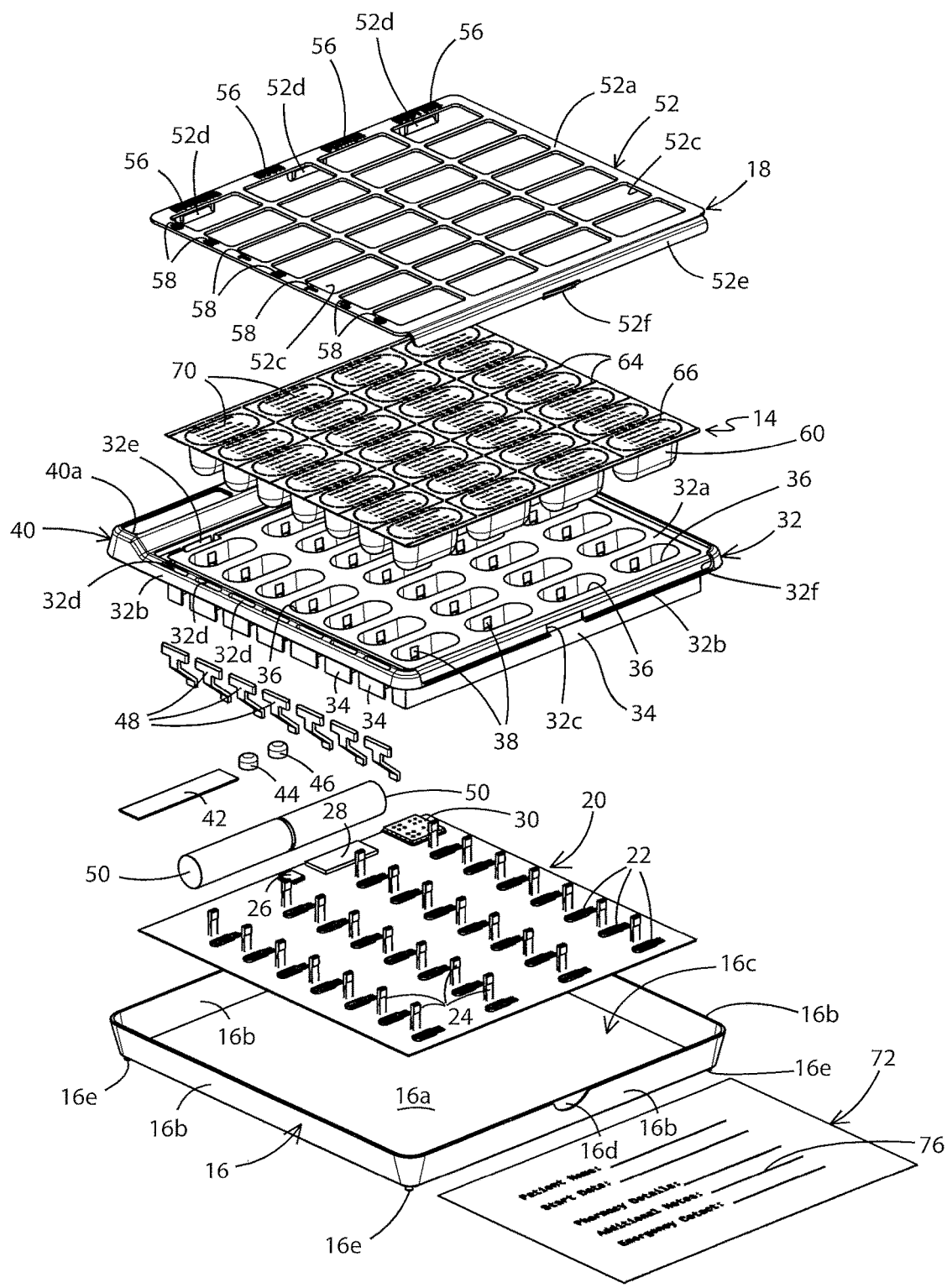
FIG. 5 is an exploded perspective view of the pill box and prefilled blister pack in accordance with an aspect of the invention.
Figure 6:
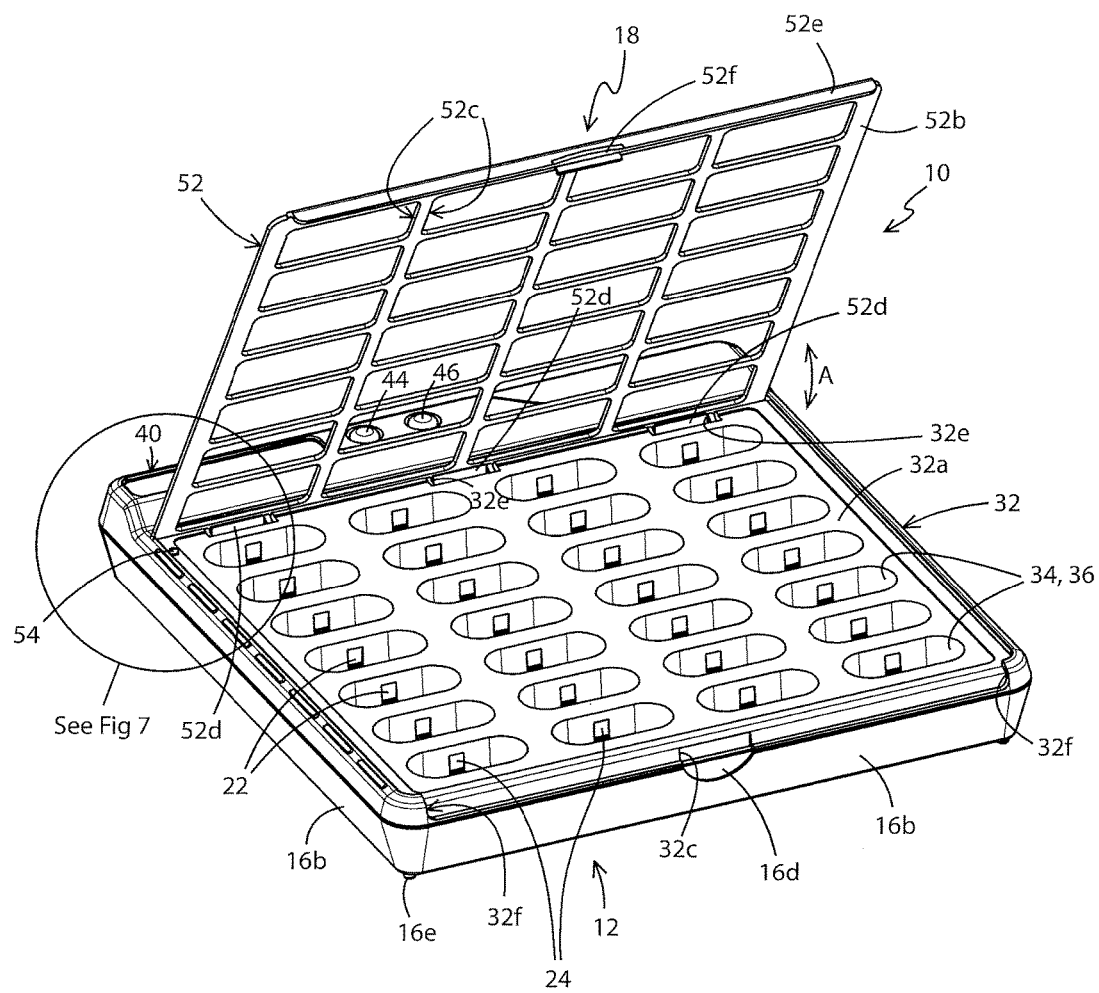
FIG. 6 is a first perspective view of the pill box in a second position; showing the pill box in an open position and without a prefilled blister pack loaded therein.
Figure 7:
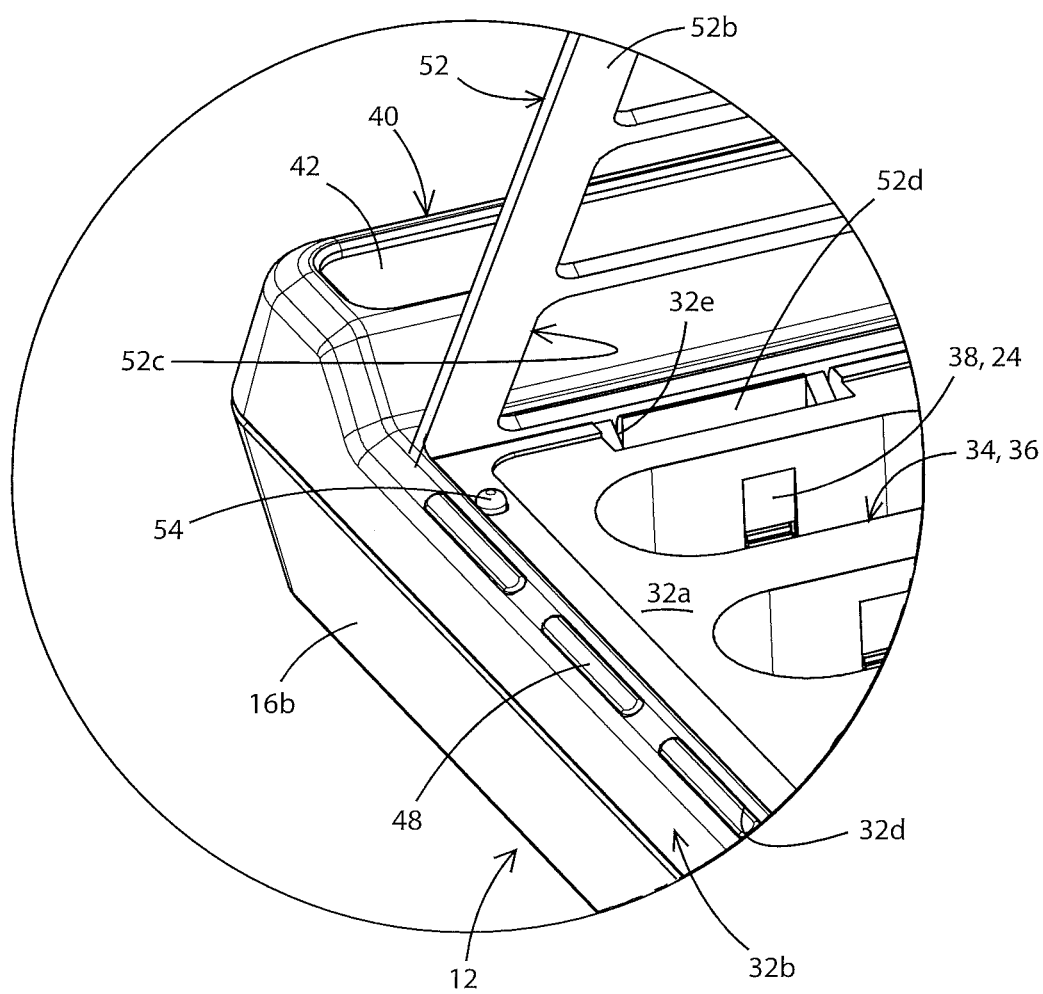
FIG. 7 is an enlargement of the highlighted region of FIG. 6.
Figure 11:
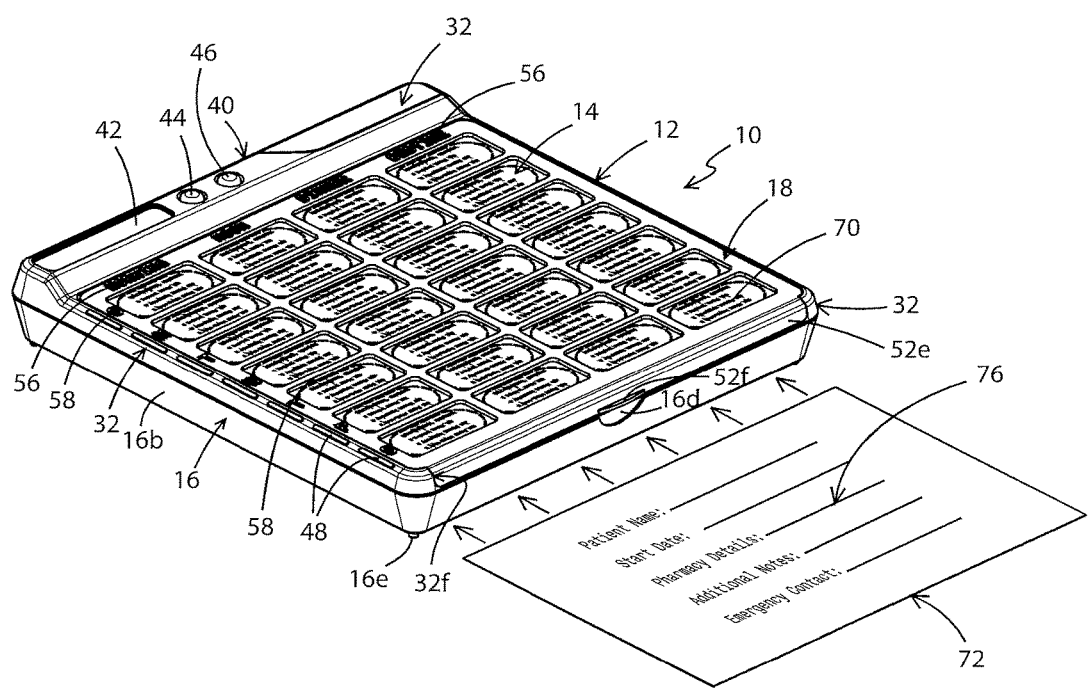
FIG. 11 is a perspective view of the pill box in a closed position and showing the prefilled blister pack loaded therein; and showing the patient information card being positioned for storage within the base of the pill box.
Figure 12:
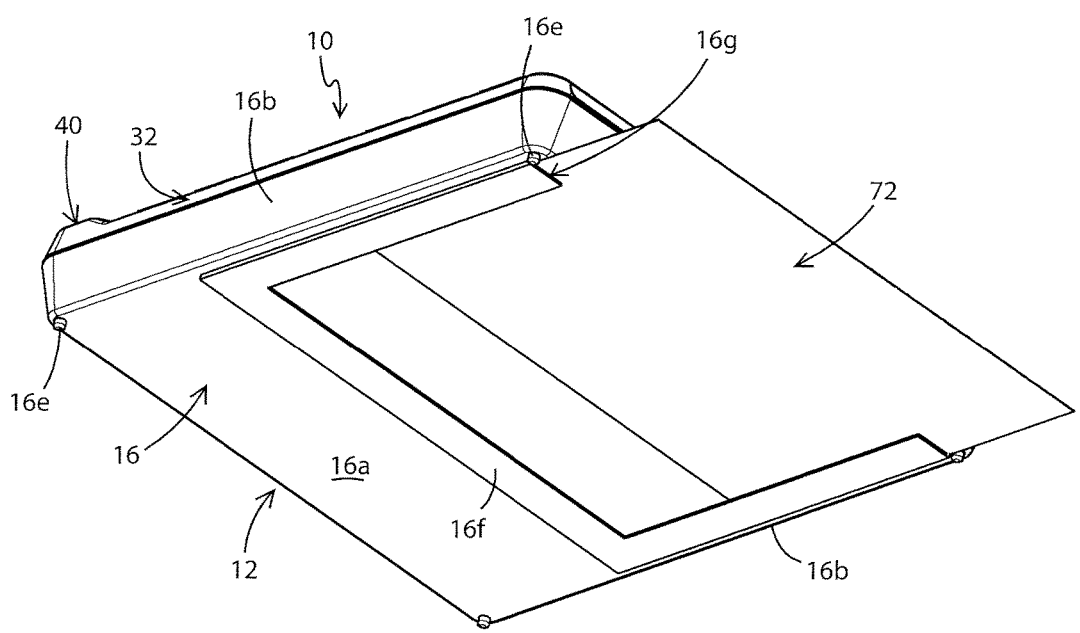
FIG. 12 is a bottom perspective view of the pill box of FIG. 11 with the patient information card partially retained in a storage frame of the pill box.
Figure 13:
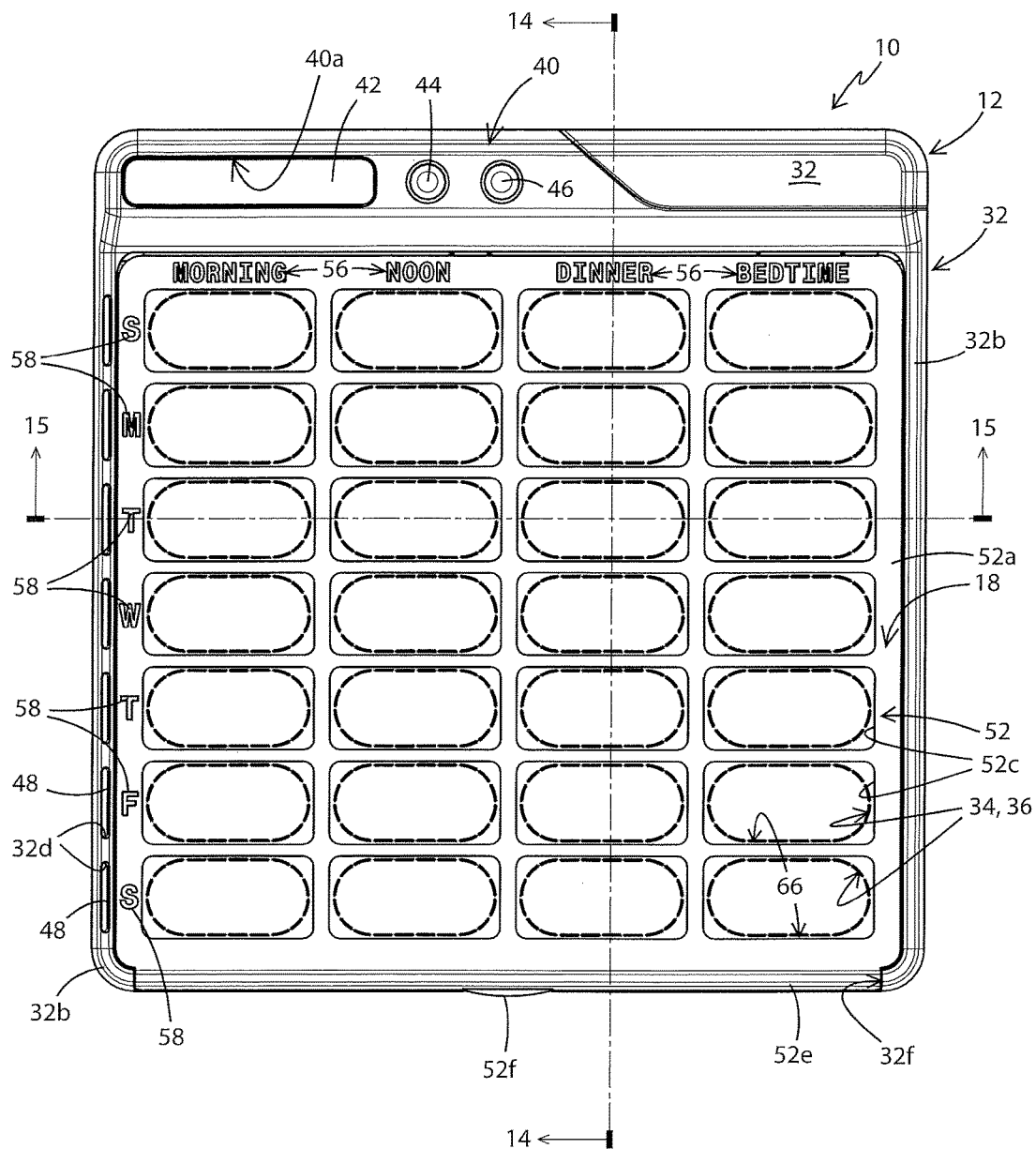
FIG. 13 is a top view of the pill box with information regarding the patient and dosing instructions removed from the blister pack so that the shape of the various components may be more readily seen.

Referring still to FIGS. 1-16 and particularly to FIG. 5, housing 12 a base comprising a bottom region 16 and a top region 32 and a grid 18 that is engaged with the base. Lower region 16 includes a bottom wall 16a (FIG. 5) and a peripheral wall 16b that extends outwardly and upwardly from a perimeter of bottom wall 16a. Bottom wall 16a and peripheral wall 16b bound and define a compartment 16c. A generally semi-circular depression 16d is defined in a front region of peripheral wall 16b. A plurality of feet 16e extends outwardly and downwardly from an exterior surface of bottom wall 16a. Feet 16e, when placed on a surface, will hold bottom wall 16a a short distance above the surface. As best seen in FIG. 12, a U-shaped frame 16f is provided on the exterior surface of bottom wall 16a. A gap 16g is defined between the exterior surface of bottom wall 16a and an interior surface of frame 16f. Frame 16f may open toward (i.e., be accessible from) the front region of peripheral wall 16b or in any other direction. The purpose of frame 16f and gap 16g will be described later herein.

Figure 15:
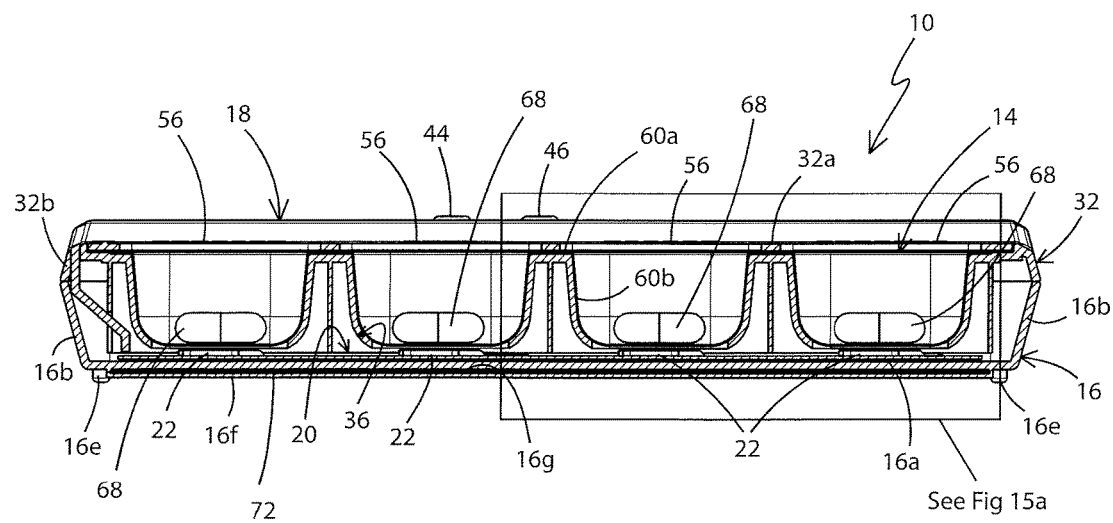
FIG. 15 is a lateral cross-section of the pill box taken along line 15-15 of FIG. 13.
Figure 15A:
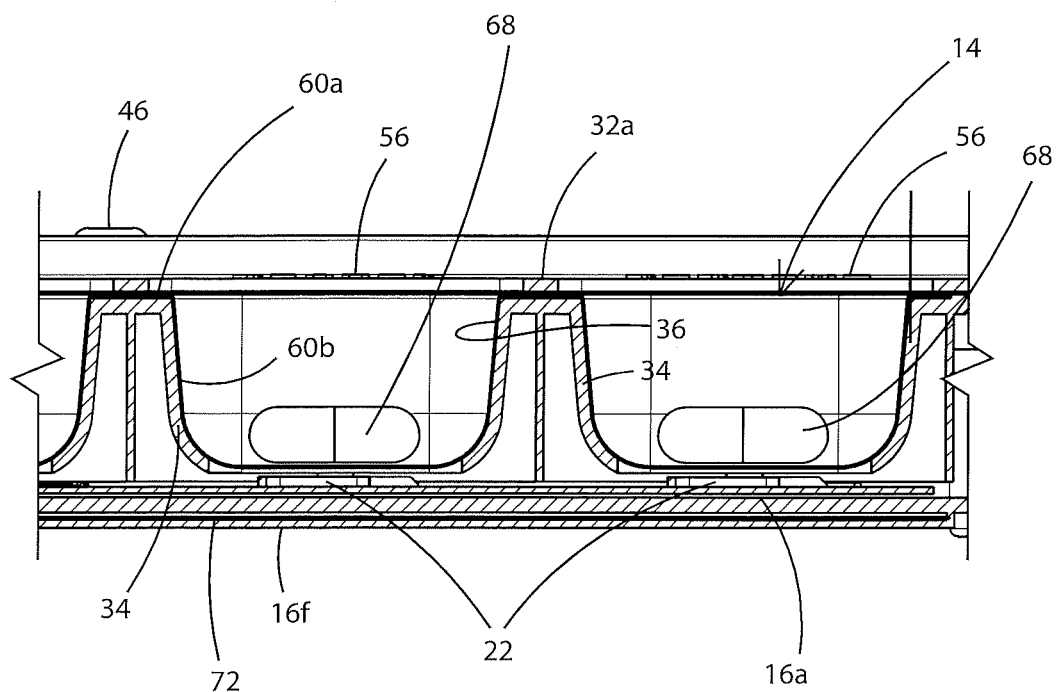
FIG. 15a is an enlargement of the highlighted region of FIG. 15.
Figure 16:
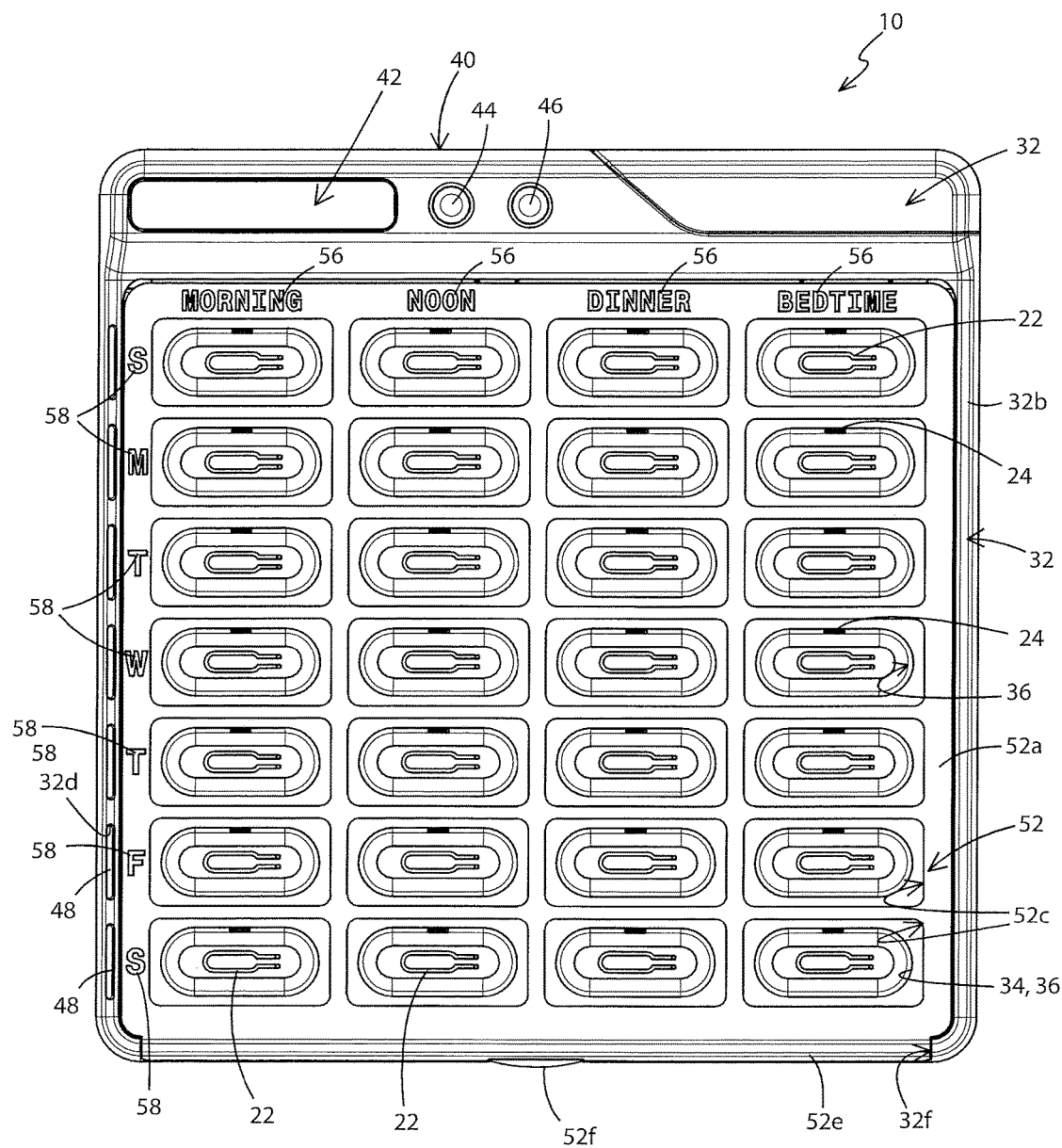
FIG. 16 is a top view of the pill box with the prefilled blister pack and interior coating layer removed therefrom and showing the capacitance sensing loops on the printed circuit board.

A printed circuit board (PCB) 20 is received in compartment 16c of lower region 16. PCB 20 includes a flat sheet 20a onto which a plurality of components are mounted. Sheet 20a is sized to be received within compartment 16c and to be positioned adjacent the interior surface of bottom wall 16a of lower region 16. The first components mounted on sheet 20a of PCB 20 are a plurality of capacitance sensing loops 22 (FIGS. 5, 6 and 14-16) or sensors that utilize a CRS input. Each sensing loop 22 comprises a wire trace loop positioned on an exterior surface of the PCB 20 and generally parallel thereto. Each loop 22 may be formed into a generally U-shaped configuration (FIG. 16). Sensing loops 22 may be arranged in rows and columns on PCB 20 and covered by some type or protective film to protect them. (FIG. 16 shows the configuration of the various sensing loops 22 with that protective film removed so that the loops 22 may be more readily seen.) FIG. 16 shows that loops 15 are arranged in four columns and seven rows. When PCB 20 is engaged in lower region 16 the columns extend from the front region of lower region 16 toward the back thereof and the rows extend from one side region of the lower region 16 to the other. It will be understood that while PCB 20 is illustrated as having twenty-eight loops 22 therein, a different numbers of loops 22 may be utilized instead. The number of loops 22 utilized in PCB 20 is dictated by the blister pack 14 which is to be engaged therewith.

A second type of component mounted onto PCB 20 is a plurality of LEDS (light emitting diodes) 24. Each LED 24 is positioned proximate one of the sensing loops 22. LEDs 24 may be arranged so that each LED 24 is located between a pair of adjacent sensing loops 22. LEDs 24 are therefore also arranged in a pattern and may be provided in rows and columns that substantially match the rows and columns of sensing loops 22. As a result, twenty-eight LEDs 24 are provided on PCB 20. Again, the number of LEDs 24 utilized in pill box 10 is dictated by the blister pack 14 which is to be engaged with housing 12. LEDs 24 may be mounted so that they extend vertically upwardly from the flat exterior surface of PCB 20. LEDs 24 may emit multi-colored light or may emit a single color of light.

Additional components that may be provided on PCB 20 are an accelerometer 26, a SIM card 28 (i.e., a Subscriber Identity Module card) and a central processing unit (CPU) 30. CPU 30 includes a microprocessor and programming relating to the medication reminder and compliance system and to the operation of the various components of that system. Loops 22, LEDs 24, accelerometer 26 and SIM card 28 are all operatively engaged with CPU 30. Accelerometer 26 detects movement of pill box 10. If, for example, pill box 10 is picked up, the accelerometer 26 will detect that movement and sensing by the loops 22 is then halted until pill box 10 is stable and stationary once again. SIM card 28 enables bi-directional direct communication of pill box 10 with a remote electronic device such as a cell phone, a smartphone, a personal computer, a tablet, or a pager by way of cellular, Wi-Fi or Bluetooth technology. Other components may also be mounted on PCB 20 and operatively engaged with CPU 30. For example, a speaker for generating an alarm or warning sound may be mounted on PCB 20 or on some other part of housing 12.

Figure 14:
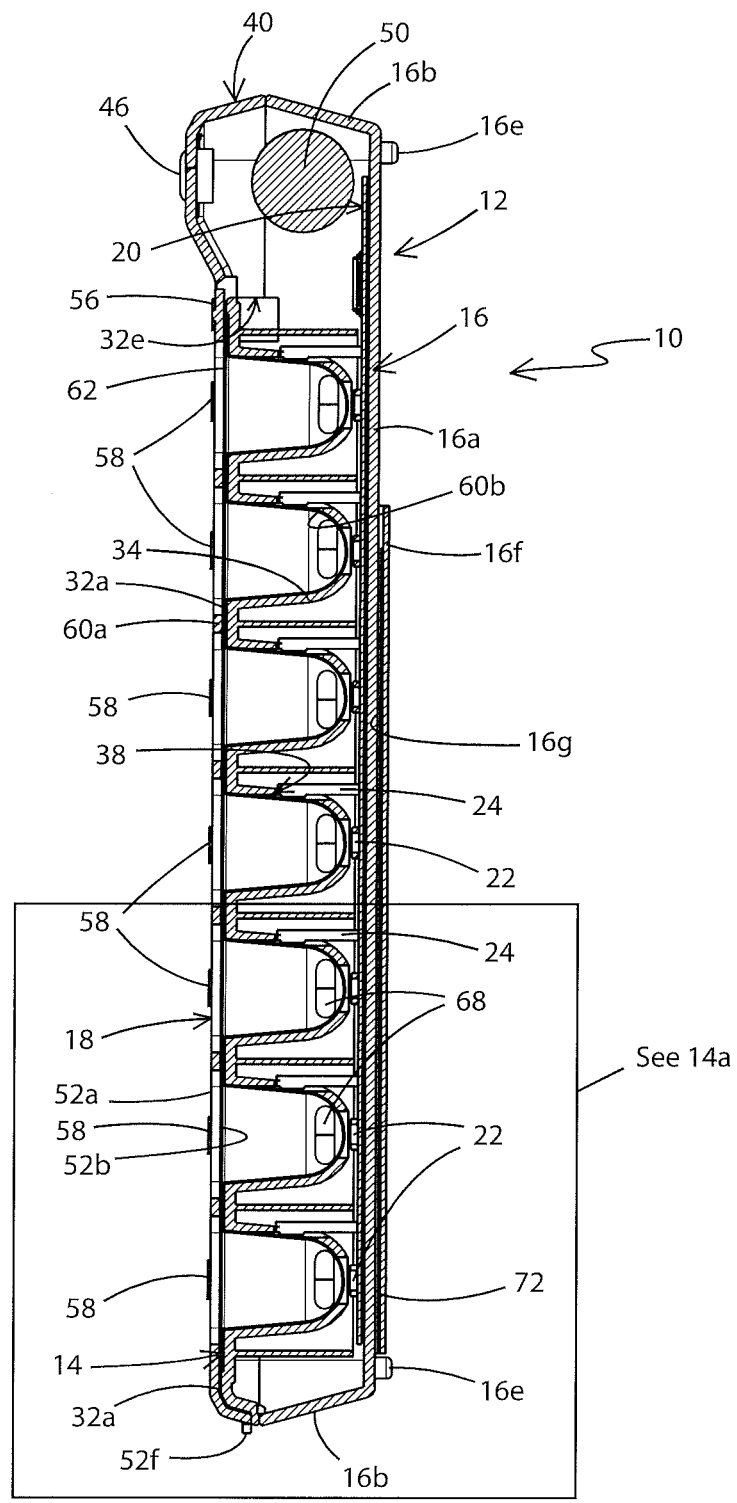
FIG. 14 is a longitudinal cross section of the pill box taken along line 14-14 of FIG. 13.
Figure 14A:
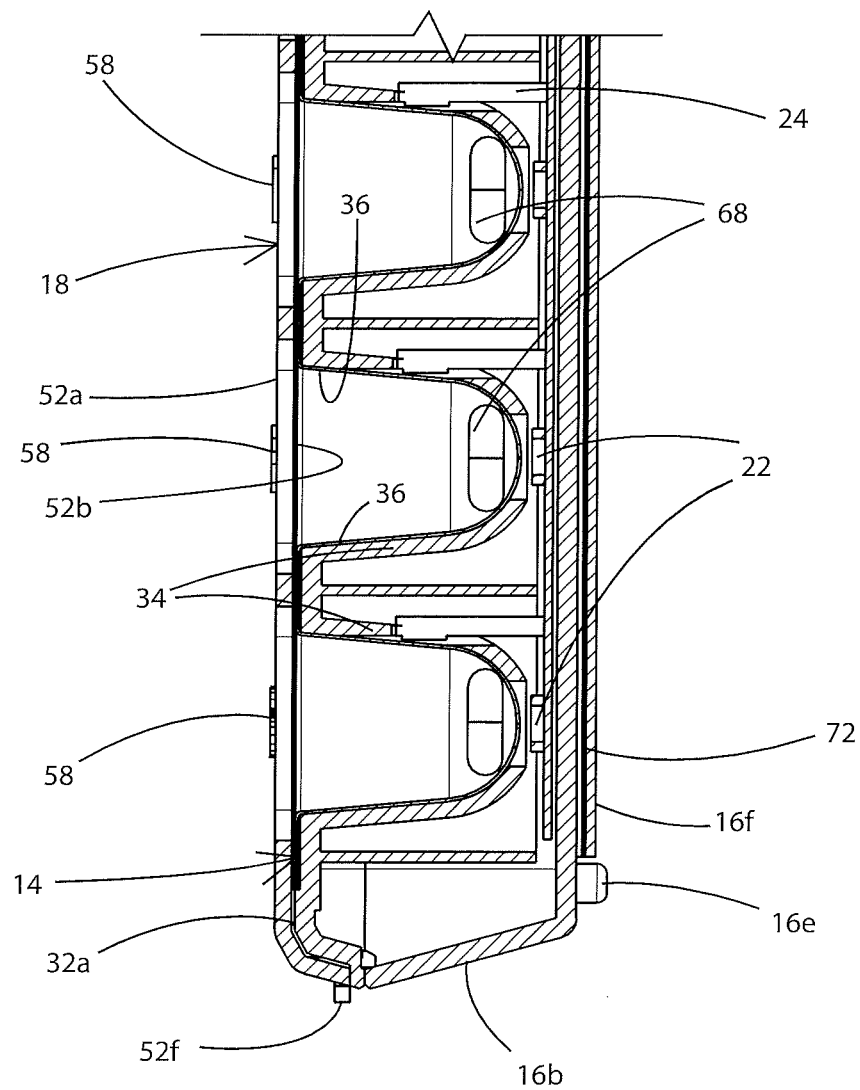
FIG. 14a is an enlargement of the highlighted region of FIG. 14.

Housing 12 further comprises a top region 32 that is designed to fit onto lower region 16 and close off access to compartment 16c. Top region 32 thereby protects PCB 20 and the components engaged therewith. Top region 32 also provides a platform for receiving and supporting blister pack 14 within housing 12. Referring to FIG. 5, top region 32 includes a top wall 32a and a peripheral wall 32b that extends outwardly and downwardly from top wall 32a. Peripheral wall 32b is complementary in size to the interior length and width of peripheral wall 16b of lower region 16 and is designed to fit onto lower region 16 so that peripheral walls 32b and 16b are substantially flush. A plurality of discrete chambers 34 are provided in top wall 32a and extend into compartment 16c. Each chamber 34 extends outwardly and downwardly from a lower or interior surface of top wall 32a. These chambers 34 may be oriented in substantially parallel rows and spaced laterally from each other. Top wall 32a defines an opening 36 to each chamber 34. Chambers 34 and thereby the openings 36 thereto may be arranged in a plurality of rows and columns. As illustrated in FIG. 5, there may be four rows of seven chambers 34 extending downwardly from top wall 32a and therefore four rows of seven openings 36 defined in top wall 32. An inner side surface of each chamber 34 defines a depression 38 therein that is complementary in shape and size to at least part of one of the LEDs 24. When PCB 20 is located within lower region 16 and top region 32 is engaged with lower region 16, each LED 24 is received within a depression 38 of one of the plurality of chambers 34. The LEDs 24 may be multi-colored LEDs and are positioned in such a way within the chambers 34 that light emitted therefrom is substantially prevented from shining into the surrounding chambers 34. In other words, light from one LED 24 will not spill over into adjacent chambers 34. Thus, when a blister pack 14 is engaged with housing 12 an illuminated LED 24 will only illuminate a specific region of that blister pack 14 and thereby indicate to a patient or caregiver which part of the pack 14 to access for a next dose of medication. The light of an illuminated LED 24 is sufficiently strong enough to shine through the portion of the blister pack 14 within a particular chamber 34 and thereby be visible to the patient or caregiver. FIGS. 14 and 15 illustrate how the LED's 24 are arranged so that the light thereof is blocked off from adjacent openings 36 and thus only serve to illuminate the particular chamber 34 within which a particular LED 24 is located.

A section of the PCB 20 including one of the loops 22 is located adjacent a bottom region of each chamber 34. In this way each loop 22 is only able to detect the presence or absence of medication in the specific chamber below which the loop 22 is located.

Top region 32 defines a slot 32c in a curved front region of peripheral wall 32b. Slot 32c is generally centrally located within the front region and is vertically aligned with depression 16d in lower region 16 when top region 32 and lower region 16 are engaged with each other. Top region 32 further includes a control panel region 40 that is on an opposite side of top region 32 from slot 32c. Control panel region 40 is of a greater thickness than the rest of top region 32 and defines a first slot 40a (FIG. 5) for an LCD display 42; a pair of holes 40b, 40c for control buttons 44, 46. LCD display 42 will display messages generated by CPU 30 thereon. These messages may include dosing instructions, reminders or warnings for the patient or caregiver. Although not illustrated herein, pill box 10 may also include a device for generating audible alarms that is linked to CPU 30. When reminders or warnings are sent by the CPU 30 to display 42, an audible reminder or warning sound may also be generated to alert the patient or caregiver. The sounds aid in prompting the patient or caregiver to read information displayed on display 42. CPU 30 will also cause individual LEDs 28 to be illuminated to visually indicate which part of pill box 10 to access in order to take a next dose of the medication retained therein.

A plurality of slots 32*d* is defined at intervals along a side region of top region 32. Each slot 32*d* is laterally aligned with a row of openings 36 and receives one of a plurality of lightpipes 48 therein. Pill box 10 is provided with a power supply and, as illustrated in FIG. 5, that power supply may comprise one or more batteries 50 that are housed beneath the raised control panel region 40 and are operatively engaged with all of the components within pill box 10 that require power. Wiring between batteries 50 and the components that require power, such as lightpipes 48, is omitted for clarity of illustration. A plurality of depressions 32*e* (FIGS. 5 and 6) is defined in top wall 32*a* at the base of control panel region 40. Depressions 32*e* are spaced a distance apart from each other and are aligned laterally. Curved front region of peripheral wall 32*b* further defines a recess 32*f* (FIG. 5) therein. Recess 32*f* extends for substantially the entire length of the front region and slot 32*c* is defined within a generally central area of recess 32*f*.

Figure 8:
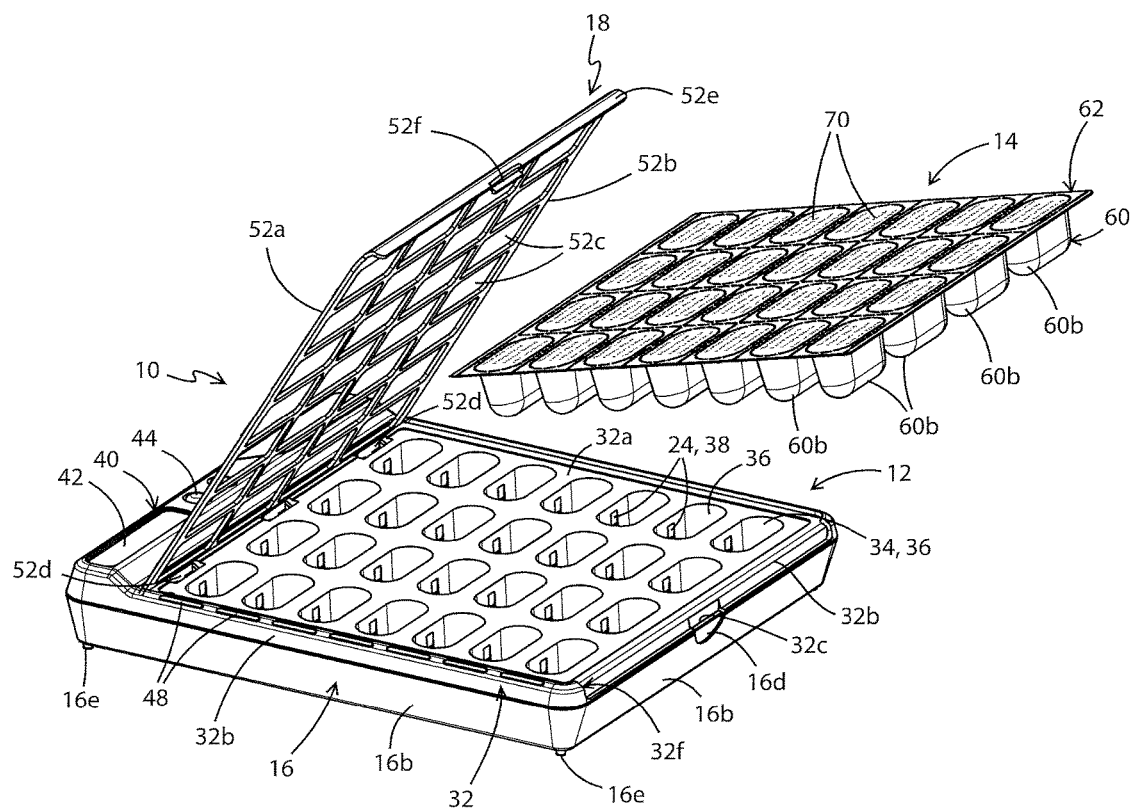
FIG. 8 is a second perspective view of the pill box in an open position and with the prefilled blister pack exploded therefrom.

As indicated earlier herein, pill box 10 further comprises a capture grid 18 that is pivotally engaged with top region 32. Grid 18 comprises a wall 52 having an exterior surface 52*a* (FIG. 5) and an interior surface 52*b* (FIG. 8). Wall 52 defines a plurality of apertures 52*c* therein which extend between exterior and interior surfaces 52*a*, 52*b* of wall 52. Each aperture 52*c* is positioned to align with one of openings 36 in top region 32 when grid 18 is moved to a closed position relative to lower region 16, 32. over top wall 32*a*. The closed position is illustrated in FIG. 1.

Grid 18 includes a plurality of flanges 52*d* (FIG. 5) that extend outwardly and downwardly from interior surface 52*b* of wall 52. Flanges 52*d* are laterally aligned with each other and spaced a distance apart. Each flange 52*d* is configured to be received in one of the depressions 32*e* defined in top wall 32*a* of top region 32. Flanges 52*d* are configured to interlock within the associated complementary depressions 32*e* and in such a way that grid 18 may be rotated about an axis extending along the laterally aligned flanges 52*d*. This interlocking engagement between grid 18 and top region 32 enables lid to pivot in the manner indicated by arrow "A" in FIG. 6 between the open position (FIG. 6) and the closed position (FIG. 1). A closure sensor 54 (FIG. 7) is provided adjacent the region where grid 18 is pivotally engaged with top wall 32*a*. Closure sensor 54 is provided to indicate when grid 18 is in a fully closed position. Closure sensor 54 is in electronic communication with CPU 30.

A front region 52*e* of grid 18 is convexly curved and is complementary to the curved front region of peripheral wall 32*b* of top region 32. The front region 52*e* of grid 18 is configured to be received in recess 32*f* when grid 18 is pivoted into the closed position. A latching mechanism 52*f* is provided centrally on front region 52*e*. Latching mechanism 52*f* is configured to be received in slot 32*e* of top region 32 and thereby latch grid 18 to top region 32, capturing blister pack 14 therebetween. Latching mechanism 52*f* overhangs slot 32*c* and depression 16*d* and the slot and depression 32*c*, 16*d* therefore provide a placed on pill box 10 where a person may insert a fingertip to raise grid 18. Closure sensor 54 detects when grid 18 is closed and latched and transmits this information to CPU 30. Latching the grid 18 to top region 32 and lower region 16 helps to hold blister pack 14 in close proximity to sensing loops 22 on PCB 20. This ensures that more accurate sensing by sensing loops 22 may take place. The latching of grid 18 also more firmly supports the flimsier blister pack 14 when pack 14 is contacted by the patient or caregiver to remove medication therefrom. When grid 18 is closed and latched then the pill box 10 is activated as a reminder system.

Grid 18 is provided with a plurality of indicia or markings thereon. First indicia, represented by the reference number 56, are each provided on exterior surface 52*a* of wall 52 in a position that aligns the first indicia 56 with one of the columns of apertures 52*c*. Second indicia, represented by the reference number 58, are each provided on exterior surface 52*a* of wall 52 in a position that aligns the second indicia 58 with one of the rows of apertures 52*c*. First indicia 56 may represent a time of day for taking medication as is indicated by the terms "Morning", "Noon", "Dinner" and "Bedtime" marked on grid 18. Different first indicia 56 may be utilized such as actual times such as "6 am", "12 pm" etc. Second indicia 58 may represent days of the week. As illustrated on grid 18, second indicia 58 may include the first letter of each day of the week such as "S" for Sunday, "M" for Monday etc. Alternatively, the full word for the day of the week may be provided as the second indicia 58. As indicated earlier herein, lightpipes 48 are laterally aligned with a row of openings 36. Consequently, since second indicia 58 are also aligned with a row of openings 36, a lightpipe 48 is aligned with each of the second indicia 58. When pill box 10 is activated and a preset time arrives for taking medication from one of the chambers 34 (as will be hereinafter described), the associated lightpipe 48 will become illuminated to indicated to the user which row of medication they are to access for that day. Although not illustrated herein it will be understood that lightpipes may also be provided which align with each column of openings 36 and thereby with first indicia 56. In that instance when it is a specific preset time of day for taking medication, the appropriate lightpipe associated with the relevant first indicia 56 will become illuminated so that the user can determine which chamber 34 to open to access their medication for that time of day.

In accordance with an aspect of the present invention, pill box 10 is filled with medication by engaging a prefilled blister pack 14 with housing 12. Blister pack 14 is shown in greater detail in FIGS. 5, 8, 9 and 10. Blister pack 14 comprises a tray 60 and a cover 62. Tray 60 may be molded from plastic and comprises a top wall 60*a* (FIGS. 14 and 15) into which a plurality of individual vials 60*b* are formed. Blister pack 14 may be provided with twenty-eight vials 60*b* that are arranged into four columns and seven rows. Blister pack 14 may therefore be pre-loaded with sufficient medication for twenty-eight dosing events, one for each vial 60*b*. It will be understood that blister pack 14 and the pill box 10 with which it is designed to be engaged, may be configured to have fewer than twenty-eight vials 60*b* or more than twenty-eight vials 60*b* and thereby be able to contain less or more medication for fewer or more dosing events.

Vials 60*b* are shaped and sized to be received within the complementary number of openings 36 defined in top wall 32*a* of top region 32. When so received, the top wall 60*a* of blister pack 14 is located adjacent exterior surface of top wall 32*a*. Vials 60*b* extend downwardly through openings 36 and into chambers 34, such that the lowermost part of each vial 60*b* is positioned adjacent one of the loops 22 on PCB 20. Vials 60*b* may have a U-shaped profile (see FIGS. 14 and 15) and therefore have a rounded bottom region. This shape ensures that the medication 68 retained within vial 60*b* is retained within a tighter area of vial 60*b* and is thus also more closely positioned proximate the associated loop 22 on PCB 20. This placement enhances the sensing ability of loop 22 to detect if medication is retained in the associated vial 60*b*.

Blister pack 14 is provided with a cover 62 that extends across the openings to all the vials 60*b*. First lines of weakness 64 are defined in each of the top wall 60a and cover 62 of blister pack 14. Second lines of weakness 66 are provided in cover 62 only and these second lines of weakness 66 are aligned with the portion of the top wall 60a which defines an opening to each vial 60b. So, the user may break one or more covered vials 60b from blister pack 14 by tearing top wall 60a and cover 62 along first lines of weakness 64. First lines of weakness 64 enable a user to separate one or more vials 60b from a remaining portion of blister pack 14. If the user opens grid 18 and detaches a "day tray" i.e., a row of four vials 60b, from blister pack 14 by tearing along first lines of weakness 64, then CPU 30 will detect that grid 18 has been lifted as closure sensor 54 will be triggered. CPU 30 will also detect via loops 22 that an entire row of blister pack 14 is missing and will send alerts to the patient or caregiver when each dose of medication from that day pack is to be taken. So, for example, CPU 30 will send a notification to the patient or caregiver's smartphone that the morning pill should be taken. CPU 30 will also receive and process confirmation signals from the patient or caregiver's smartphone that the morning pill has been taken.

The user may remove a specific portion of cover 62 from over a single vial 60b by tearing cover 62 along second lines of weakness 66 in order to access one or more pills 68 (FIGS. 14 and 15) or other medication retained within the associated vial 60b by the specific portion of cover 62. The rounded shape of each vial 60b makes it easier for the patient or caregiver to access medication 68 within the vials 60b. When the patient or caregiver pushes downwardly on the portion of cover 62 closing off the opening to a particular vial 60b, that portion of cover 62 will tear along the associated second lines of weakness 66. The patient or caregiver's finger will then slide along the rounded shape of the associated opened vial 60b until contact is made with the medication 68 within that vial. The medication, i.e., pills 68, is easier to remove from the vial 60b because vial 60b is free of corners and presents an smooth curved interior surface.

Figure 2:
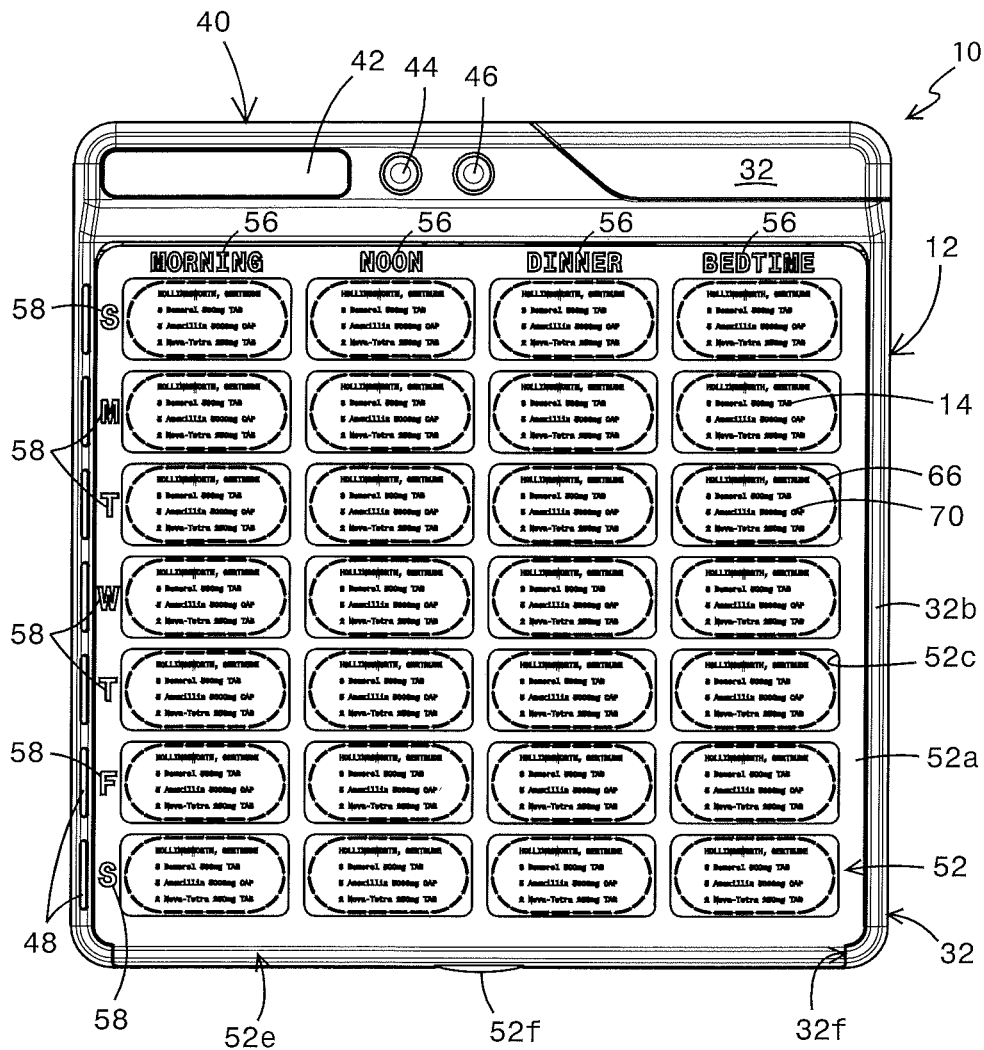
FIG. 2 is a top view of the pill box in a closed position.
Figure 3:
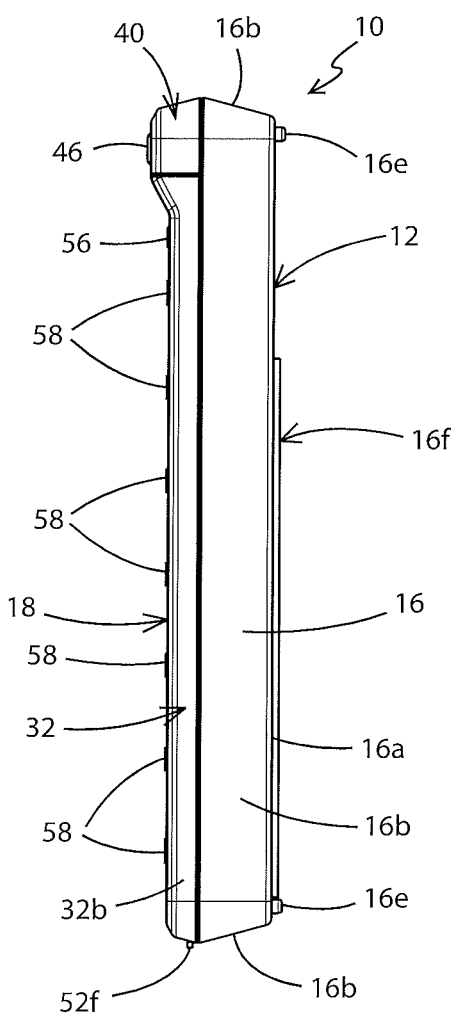
FIG. 3 is a right side view of the pill box in a closed position.
Figure 4:
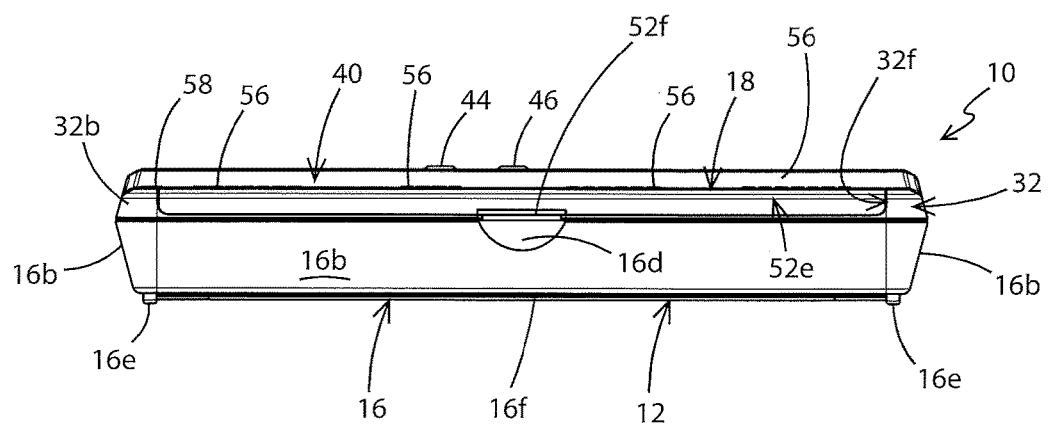
FIG. 4 is a front view of the pill box in a closed position.

As best seen in FIGS. 1 and 2, cover 62 may be imprinted with relevant information 70 that is positioned to visible through apertures 52c in grid 18 once blister pack 14 has been loaded into housing 12. The information 70 on cover 62 may relate to the medication contained within each vial 60b, the name of the patient, dosing instructions, a prescribing physician, and/or a dispensing pharmacy. So, for example, the information 70 may include the name of the patient and possibly a picture of the patient, the name of the medication within that vial 60b, the date and time the medication 68 is to be taken and whether to take pills 68 contained therein with food or water. The information 70 may also include a picture of the pills that should be loaded within a particular vial. All of this information serves to verify to the patient or caregiver what should be taken and when that medication should be taken. This aids in preventing dosing errors.

Figure 9:
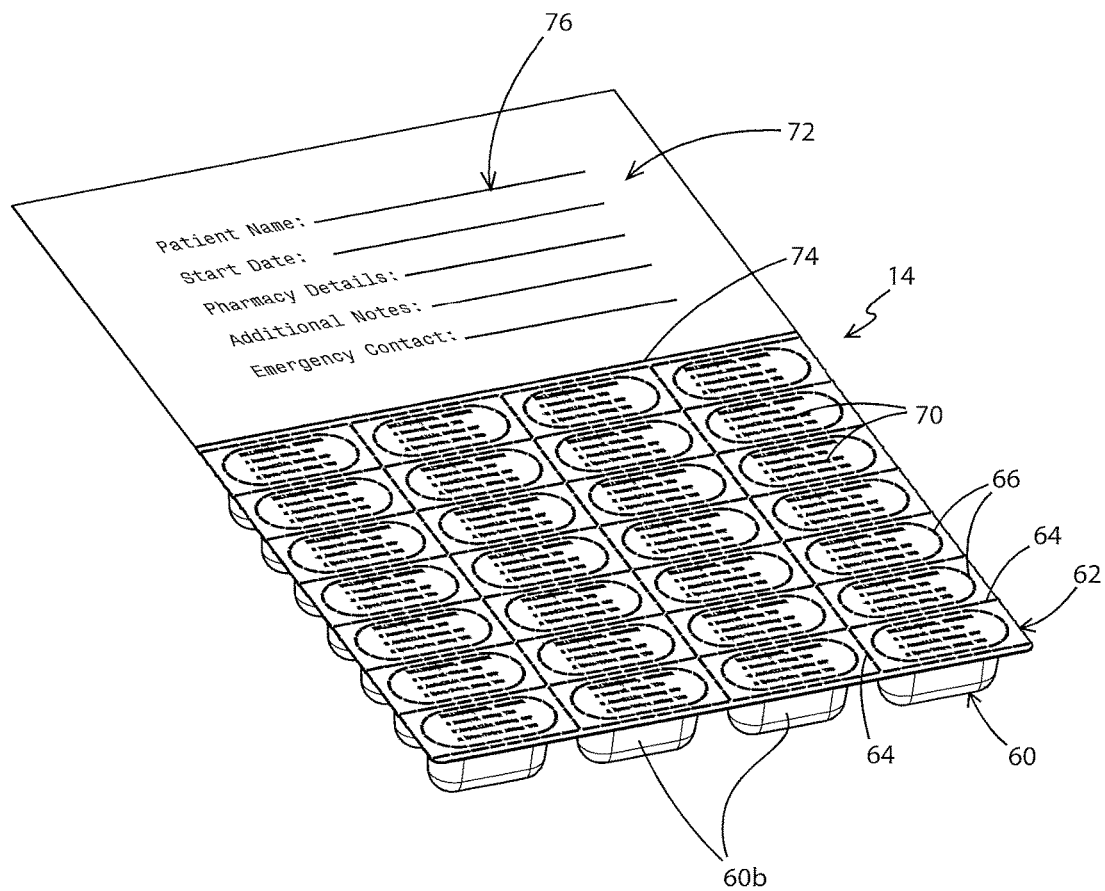
FIG. 9 is a perspective view of the prefilled blister pack shown with a patient information card attached thereto.
Figure 10:
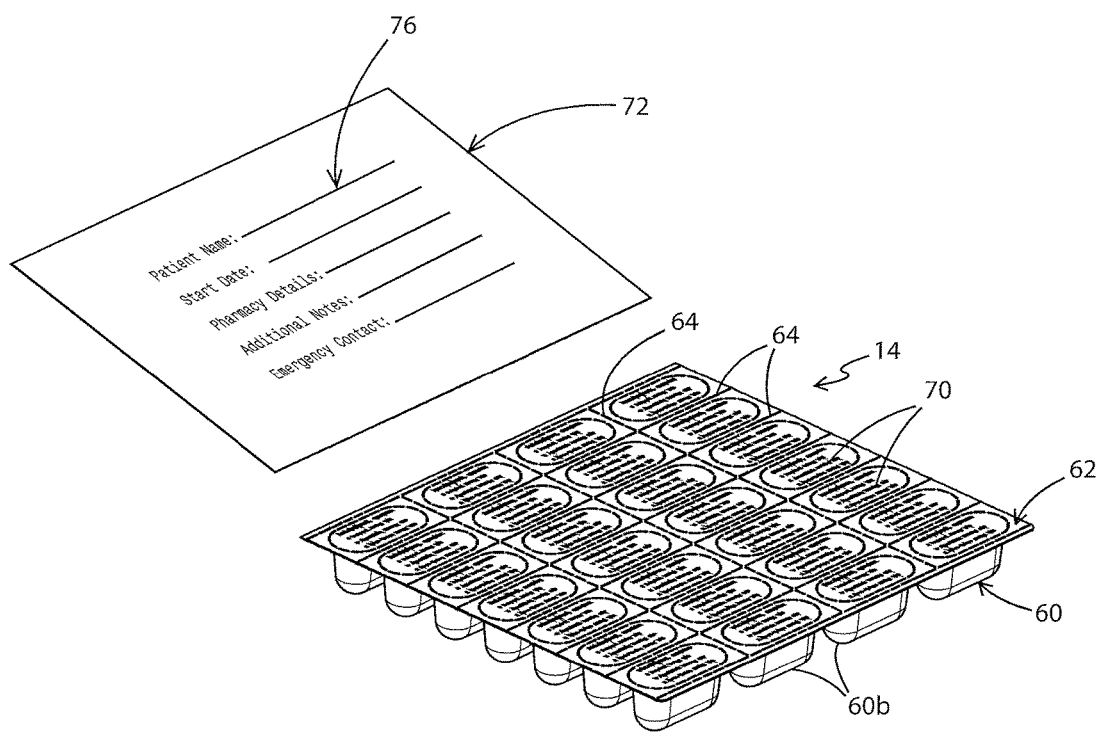
FIG. 10 is a perspective view of the prefilled blister pack of FIG. 9 with the patient information card detached therefrom.

FIGS. 9 and 10 show how the blister pack 14 may be received prior to loading of the same into pill box 10. These figures show cover 62 may include an extension that is usable as an identification card 72. Card 72 extends outwardly beyond one end of tray 60. A third line of weakness 74 (FIG. 10) may be provided between card 72 and the rest of cover 62. When blister pack 14 is shipped, card 72 may be folded about the third line of weakness 74 so that the card 72 is positioned adjacent an exterior surface of cover 62. Card 72 aids in preventing the portions of cover 62 that extend over vials 60b from being accidentally punctured. Once received by the patient or caregiver, card 72 may be detached from blister pack 14 by tearing along third line of weakness 74. Card 72 may include information 76 relating to the patient to whom the medication within blister pack 14 is to be dispensed, as well as dosing information, pharmacy contact information and emergency contact information. Any other relevant information may also be provided thereon. After card 72 is detached from blister pack 14, card 72 may be slid into the frame 16f on the underside of lower region 16. This is illustrated in FIGS. 11 and 12. Card 72 may be kept in frame 16f in case a caregiver or the patient needs to reference the information 76 contained thereon. The rest of blister pack 14 is then inserted into housing 12, grid 18 is closed and latched and then pill box 10 may be used.

CPU 30, which is operatively engaged with loops 22, constantly monitors the contents of vials 60b and can therefore detect if even one pill is removed from a particular vial 60b but other pills are left behind in that same vial. If this situation occurs, CPU 30 will generate a signal to cause an alarm to go off so as to alert the patient or a caregiver. An informational message may be displayed on display 42 alerting the patient or caregiver to the fact that some medication has not been removed from blister pack 14. An alert may also be transmitted to an electronic device connected to the pill box 10 via Wi-Fi or Bluetooth. Sounds or flashing lights may also be set off by CPU 30. When a finger is inserted into a particular vial 60b, the increased downward pressure is sensed by the associated loop 22 and that large signal change is detected by CPU 30. The signal change is interpreted by the CPU 30 as confirmation that medication 68 has likely been removed from that vial 60b.

When all of the medication 68 of blister pack 14 has been removed then grid 18 is opened, the empty blister pack 14 is removed from housing 12 and a new and prefilled blister pack is inserted into housing 12. If a new blister pack 14 is not installed within the housing 12 by the time the patient needs to take their next dose of medication, the CPU 30 will send an alert to the patient or caregiver's linked electronic device. Failure to load the new blister pack 14 within predetermined times will cause CPU 30 to generate escalating warnings to the patient and/or caregiver. CPU 30 will also cause an audible alarm to be triggered so that pill box 10 will beep for example. A message to load a new blister pack 14 will also be generated and displayed on LCD display 42.

In addition to the medication 68 retained within blister pack 14, CPU 30 may be programmed to remind a patient when to use or take other medication that is not kept within pill box 10. For example, the patient may be required to use an inhaler or a medicated cream. CPU 30 may be programmed to alert the patient or caregiver that it is time to use that inhaler or apply the medicated cream. The patient or caregiver will have to send a confirmation back to the pill box 10 from their associated electronic device that the inhaler has been used or the medicated cream has been applied. If no such confirmation is received, then pill box 10 will display a reminder on LCD display 42 and/or generate a sound or become illuminated so as to alert the patient or caregiver.

A method of dispensing medication to a patient thus comprises providing a pill box 10 including a housing 12 comprising a lower region 16, 32 and a grid 18 engageable with lower region 16, 32; and a microprocessor 30 including programming that includes a reminder schedule and a real time tracker; providing a blister pack 14 having a plurality of vials 60b defined therein with at least some of vials 60b being prefilled with medication 68 (FIG. 14); and having a cover 62 extending across openings to the plurality of vials 60, said cover 62 having lines of weakness 66 proximate each vial 60; positioning blister pack 14 in the lower region 16, 32 between top wall 32a and grid 18; engaging grid 18 with lower region 16, 32; capturing blister pack 14 between grid 18 and lower region 16, 32; and activating microprocessor 30 to initiate the reminder schedule programmed therein.

The method of dispensing medication also includes illuminating one of the vials 60b from which medication 68 is to be withdrawn in accordance with the reminder schedule. The method further includes removing a portion of cover 62 from over the illuminated vial 60b by tearing along the lines of weakness 66 proximate the illuminated vial; and removing medication 68 from the illuminated vial. The method further includes issuing an alert if a portion of cover 62 is not removed from over the illuminated vial 60b and the medication 68 is not removed from that illuminated vial 60b after a preset period of time. The step of issuing the alert includes sending an electronic communication from microprocessor 30 to an electronic device of the patient or a caregiver of the patient and/or displaying an alert message on a display 42 on housing 12; and/or emitting an audible sound from housing 12.

The method of dispensing medication 68 from housing 12 may further include providing an information card 72 extending outwardly from cover 62 of blister pack 14, separating information card 72 from cover 62 along line of weakness 74, and engaging information card 72 in a frame 16f provided on housing 12.

The method further comprises prefilling blister pack 14 with medication 68 at a factory and shipping the prefilled blister pack to the patient or to a caregiver or to a medical treatment facility.

The method may further include providing information 70 relating to medication 68 contained within blister pack 14 or a name of a patient to whom medication 68 is to be dispensed or dosing instructions relating to the medication 68 on an exterior surface of cover 62. The information 70 may be marked at repeated intervals on cover 62; wherein each interval corresponds to a position of one of the plurality of vials 60b provided in blister pack 14. Grid 18 is provided with a plurality of openings 52c defined therein and openings 52c are located so as to align with one of vials 60b defined in the blister pack 14; and when grid 18 is closed over blister pack 14, openings 52c align with vials 60b and information 70 provided at intervals on cover 62 and that information 70 is readable through the grid openings 52c.

The method further includes sensing with a sensor 22 located proximate the illuminated vial 60b whether or not medication 68 has been removed from that illuminated vial 60.

The method further includes removing a section of the blister pack 14 from a remaining portion of the blister pack along a line of weakness 64 and carrying that removed section of the blister pack 14 in a pocket or purse. The removed section may include a single vial 60b or a plurality of vials 60b (such as a sufficient number of vials for an entire day's worth of medication 68 and an entire week's worth of medication.) The method may further include issuing reminders to the patient or to a caregiver of the patient to take medication from the one or more vials detached from the blister pack at programmed intervals.

It will be understood that illuminating lightpipes 48 in conjunction with illuminating LEDs 24 and the information regarding days of the week 58 and time of day 56 provided on grid 18, all help a patient or caregiver verify which vial 60b to access in order to obtain a present dose of medication 68. Applications '966 and '037 explain in detail how the electronic reminder system of pill box 10 functions and so that reminder system will not be further described herein.

The method may further include issuing, from microprocessor 30 in housing 12 a reminder to take medication not retained within blister pack 18. This medication may include such other medications as a dose from an inhaler or the application of a topical cream. The step of issuing this reminder may include sending an alert to an electronic device of the patient's or an electronic device of a caregiver; or displaying the alert on a display screen 42 on housing 12.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A medication reminder and compliance system comprising:
   a pill box including:
      a housing;
      a microprocessor including programming that includes a reminder schedule and a real time tracker;
      a blister pack selectively receivable within the housing; said blister pack including a plurality of vials, each vial being prefilled with medication; and
      a plurality of capacitance sensors provided in the housing, wherein each sensor is located so as to be positioned adjacent a bottom wall of a different one of the vials of the blister pack when the blister pack is received within the housing; and wherein each capacitance sensor is operatively engaged with the microprocessor
   wherein the housing includes a plurality of discrete chambers, each chamber being configured to received one of the vials from the blister pack therein;
   wherein each sensor is located in the one of the chambers; and
   wherein each chamber has a bottom wall and the associated sensor is located in the bottom wall.

2. The system as defined in claim 1, wherein each vial of the blister pack is U-shaped in cross-section.

3. The system as defined in claim 1, wherein each vial of the blister pack has a lower region that is free of corners and is rounded.

4. The system as defined in claim 3, wherein the sensor associated with each vial is located beneath the lower region thereof.

5. The system as defined in claim 1, further comprising a plurality of LEDs, and wherein each LED is positioned to selectively illuminate one of the vials in the blister pack.

6. The system as defined in claim 5, wherein the housing includes a plurality of discrete chambers and each chamber includes one of the plurality of LED's, and the LED in each chamber illuminates only the chamber in which that LED is located.

7. The system as defined in claim 1, wherein the housing includes a base and a grid pivotally engaged with the base; and wherein the blister pack is positionable between the base and the grid.

8. The system as defined in claim 7, further comprising a closure sensor positioned between a portion of the grid and a portion of the base; and wherein the closure sensor is operatively engaged with the microprocessor and is activated when the blister pack is in the base and the grid is in a closed position relative to the base.

9. The system as defined in claim 7, further comprising a latching mechanism that latches the grid to the base when the blister pack is received within the housing.

10. The system as defined in claim 9, wherein engaging the latching mechanism causes each vial of the blister pack to be retained in close proximity to the sensor associated therewith.

11. The system as defined in claim 7, wherein the grid defines a plurality of openings therein; and wherein each opening is positioned to align with one of the vials in the blister pack when the blister pack is engaged in the base.

12. The system as defined in claim 1, further comprising an accelerometer located within the housing, said accelerometer being in operative engagement with the microprocessor.

13. The system as defined in claim 1, wherein the blister pack includes a tray having a top wall and the plurality of vials are defined in the top wall; and the blister pack further includes a cover that extends across the top wall and prevents access to the vials.

14. The system as defined in claim 13, further comprising indicia provided on an exterior surface of the cover; wherein the indicia include information relating to one or more of a patient to whom the medication within the blister pack is to be given, a pharmacy dispensing the medication within the blister pack, a prescribing physician, or dosing information.

15. The system as defined in claim 13, wherein the tray and cover include a plurality of first lines of weakness that enable one or more vials and a portion of the cover associated therewith to be detached from a remainder of the tray and cover.

16. The system as defined in claim 13, wherein the cover includes a plurality of second lines of weakness and each second line of weakness enables a section of the cover to be removed from over an associated one of the plurality of vials.

17. The system as defined in claim 13, wherein the cover includes an information card that extends outwardly from the tray; wherein a third line of weakness is provided in the cover and the information card is separable from a remaining portion of the cover along the third line of weakness.

18. The system as defined in claim 1, wherein each sensor comprises a wire trace loop.

* * * * *